(12) United States Patent
Coupard et al.

(10) Patent No.: US 10,961,489 B2
(45) Date of Patent: Mar. 30, 2021

(54) PROCESS FOR RECOVERING ALCOHOLS IN A FERMENTER

(71) Applicant: IFP Energies nouvelles, Rueil-Malmaison (FR)

(72) Inventors: Vincent Coupard, Villeurbanne (FR); Helena Gonzalez Penas, Lyons (FR); Eszter Toth, Lyons (FR); Mehdi Le Moel, Oullins (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/314,209

(22) PCT Filed: May 17, 2017

(86) PCT No.: PCT/EP2017/061801
§ 371 (c)(1),
(2) Date: Dec. 28, 2018

(87) PCT Pub. No.: WO2018/001628
PCT Pub. Date: Jan. 4, 2018

(65) Prior Publication Data
US 2019/0203162 A1 Jul. 4, 2019

(30) Foreign Application Priority Data

Jun. 30, 2016 (FR) ...................... 16 56209

(51) Int. Cl.
| | | |
|---|---|---|
| C12F 3/04 | (2006.01) | |
| C12P 7/16 | (2006.01) | |
| C12P 7/10 | (2006.01) | |
| B01D 3/14 | (2006.01) | |
| B01D 53/14 | (2006.01) | |
| B01D 3/34 | (2006.01) | |
| B01D 3/00 | (2006.01) | |
| B01D 3/36 | (2006.01) | |
| C12P 7/04 | (2006.01) | |
| C12P 7/06 | (2006.01) | |

(52) U.S. Cl.
CPC ............. *C12F 3/04* (2013.01); *B01D 3/002* (2013.01); *B01D 3/143* (2013.01); *B01D 3/343* (2013.01); *B01D 3/36* (2013.01); *B01D 53/1418* (2013.01); *B01D 53/1487* (2013.01); *C12P 7/04* (2013.01); *C12P 7/06* (2013.01); *C12P 7/10* (2013.01); *C12P 7/16* (2013.01); *B01D 2256/16* (2013.01); *B01D 2256/22* (2013.01); *B01D 2257/702* (2013.01); *B01D 2257/708* (2013.01); *B01D 2258/05* (2013.01)

(58) Field of Classification Search
CPC combination set(s) only.
See application file for complete search history.

(56) References Cited

U.S. PATENT DOCUMENTS

| 9,453,245 B2 | 9/2016 | Ropars |
| 2017/0137848 A1 | 5/2017 | Lopes Ferreira |

FOREIGN PATENT DOCUMENTS

| FR | 2974116 A1 | 10/2012 |
| FR | 3023300 A1 | 1/2016 |

OTHER PUBLICATIONS

Xue, C. et al., Biotechnol Bioengin. 2012 vol. 109, pp. 2746-2756.*
Richter, H. et al. Biotechnol and Bioeng. 2012 vol. 109, pp. 913-921.*
International Search Report PCT/EP2017/061801 dated Aug. 8, 2017. (pp. 1-3).
Thaddeus C Ezeji et al: "Improving performance of a gas stripping-based recovery system to remove butanol from Clostridium beijerinckii fermentation", Bioprocess and Biosystems Engineering, Springer, Berlin, DE, vol. 27, No. 3, Apr. 2, 2005 (Apr. 2, 2005), pp. 207-214, XP019347339, ISSN: 1615-7605.
Hanno Richter et al: "Prolonged conversion of n-butyrate to n-butanol with Clostridium saccharoperbutylacetonicum in a two-stage continuous culture with in-situ product removal", Biotechnology and BIOENGINEERING, vol. 109, No. 4, Nov. 17, 2011 (Nov. 17, 2011), pp. 913-921, XP055081864, ISSN: 0006-3592.
Chuang Xue et al: "High-titer n-butanol production by clostridium acetobutylicum JB200 in fed-batch fermentation with intermittent gas stripping", Biotechnology and Bioengineering, vol. 109, No. 11, Nov. 8, 2012 (Nov. 8, 2012), pp. 2746-2756, XP055346003, ISSN: 0006-3592.

* cited by examiner

*Primary Examiner* — Heidi Reese
(74) *Attorney, Agent, or Firm* — Millen White Zelano and Branigan, PC; Csaba Henter

(57) ABSTRACT

The present invention concerns a process for recovering fermentation products present in a fermentation mash produced in a bioreactor (9), comprising a step a) in which a gas stream (15) is sent into the fermentation mash under pressure in order to entrain at least a portion of the products and produce a gas stream (16) which is enriched in fermentation products. The process comprises a step h) for storage of the fermentation gases and the gas stream which is sent to the step a) is constituted by the stored fermentation gases.

18 Claims, 2 Drawing Sheets

PROCESS FOR RECOVERING ALCOHOLS IN A FERMENTER

Figure 1:
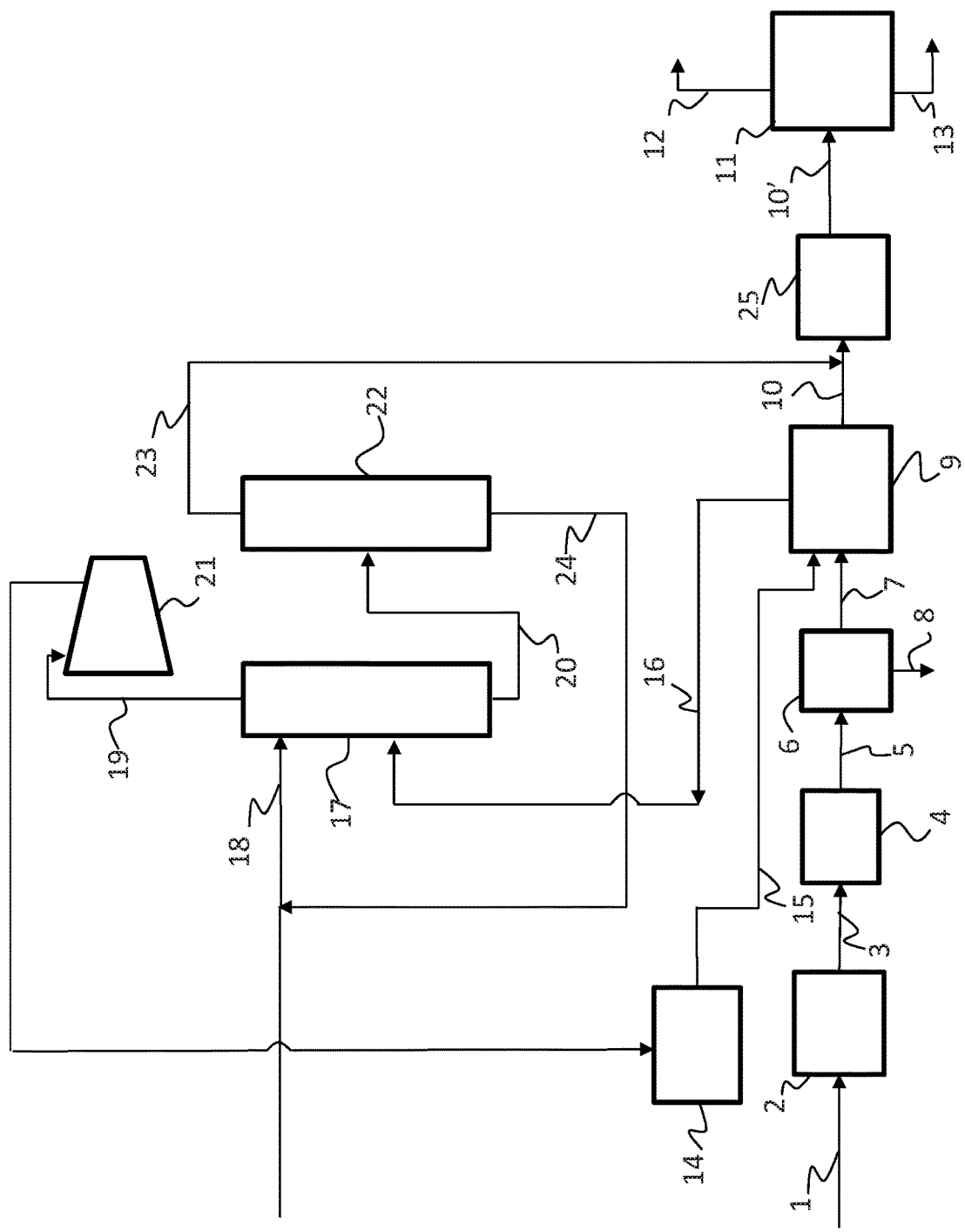

The present invention relates to a process for recovering fermentation products from a fermentation broth contained in a fermenter. The process in accordance with the invention is particularly suitable for the recovery of alcohols, esters, carboxylic acids and ketones, and aldehydes produced by fermentation of an aqueous solution of C5 and/or C6 sugars. The recovery process may in particular be applied to a fermentation process of the ABE (Acetone/Butanol/Ethanol) or IBE (Isopropanol/Butanol/Ethanol) type.

PRIOR ART

In order to meet energy transition challenges, a great deal of research has been carried out in order to develop processes termed "green", allowing access to chemical intermediates in a manner that is an alternative to oil refining and/or petrochemistry.

The alcohols obtained from fermentation (n-butanol, isopropanol) are the most promising substitutes for petrochemical derivatives. ABE (Acetone-Butanol-Ethanol) fermentation is one of the oldest fermentation processes to have been industrialized (start of the 20th century) and has since been studied in depth. IBE fermentation, producing a mixture of isopropanol, butanol and ethanol, may also be mentioned. These two types of fermentation are carried out under strict anaerobic conditions in the presence of a fermentation microorganism, generally from the genus *Clostridium*.

One of the sticking points in the development of fermentation processes is the step for recovery of the products from the highly diluted aqueous medium. This is the determining parameter as regards the economics of these types of process. In order to render large-scale fermentation production economically viable, it has proved to be necessary to maximize the final titre as well as the productivity in terms of volume in the bioreactor, these two parameters being severely restricted by marked inhibition of the microorganisms by the products of interest. It is in fact known that above a concentration in the fermentation medium, butanol has an inhibiting effect on the microorganism, for example on *Clostridium*. The use of techniques for coupling fermentation and separation (liquid extraction, adsorption, stripping, etc) means that the inhibiting products can be recovered as they are produced. These techniques offer the means for overcoming the inhibition limit imposed during microbial production, and as a consequence of reducing the energy requirement for distillation of a final, extremely diluted fermentation broth.

In situ techniques for the recovery of butanol have been explored in depth in the literature for Acetone/Butanol/Ethanol fermentation.

The recovery of products obtained from an ABE fermentation by stripping with a gas injected into the bioreactor has been proposed in the literature (Quereshi and Blaschek (Renewable Energy, 22 (4)) or Ezeji et al. (Appl. Microbio. Biotechnol., 63 (6)). In those schemes, the alcohols are recovered by condensation of the gas obtained from the reactor, which proves to be extremely costly from an energy standpoint.

Kuan-Ming & al. (Journal of the Taiwan Institute of Chemical Engineers, 45 (2014) 2106-2110) describe an integrated process coupling gas stripping and liquid-liquid extraction with oleyl alcohol in situ, i.e. inside the fermenter.

Furthermore, a scheme is known from the document U.S. Pat. No. 8,945,891 for recovering metabolites obtained from an ABE fermentation by injecting gas into the bioreactor followed by a step for recovery of the metabolite by absorption with a composition comprising isophorone as the solvent.

U.S. Pat. No. 8,460,439 describes a method for recovering butanol contained in a fermentation broth, in which a portion of the fermentation broth is sent to a stripping step employing an inert gas in a manner such as to recover a gas enriched in butanol which is then treated in an absorption section in the presence of an organic solvent, for example an alcohol containing at least 8 carbon atoms.

One aim of the invention is to propose an alternative process for recovering fermentation products present in a fermentation mash from a bioreactor which is effective, simple to carry out and for which the capital expenses (CAPEX) and operating expenses (OPEX) are optimized.

SUMMARY OF THE INVENTION

The present invention thus concerns a process for recovering fermentation products present in an aqueous fermentation broth produced in a bioreactor, which comprises a step a) in which a gas stream is sent into the aqueous fermentation broth under pressure in order to entrain at least a portion of the alcohols and produce a gas stream which is enriched in alcohols. The process in accordance with the invention is characterized by the presence of a step b) for prior storage of the fermentation gases produced in the bioreactor, which then constitute the gas stream which is sent to the bioreactor in order to entrain the fermentation products.

Hence, the process in accordance with the invention upgrades the gases produced by the fermentation, which can be considered to be by-products of the fermentation, as stripping gas in order to be able to extract the products of interest from the fermentation system. Carrying out the process thus no longer necessitates supplying gas from outside the process, which would generate non-negligible transport costs. Finally, in terms of investment, the process requires just one storage device (drum), which is in any case already necessary in the case in which the stripping gas is not produced in situ.

The process in accordance with the invention also has the advantage of allowing at least a portion of the fermentation products to be recovered using a method other than distillation, this latter being particularly energy-consuming because of the dilute nature of the products present in the fermentation mash.

The process for in situ recovery of the fermentation products can also be used to provide better control of their content in the fermentation medium, in order to limit this content to a threshold value which is still acceptable for the microorganism. In fact, it is known that beyond a certain content in the fermentation medium, the fermentation products, and particularly the alcohols (for example butanol), have an inhibiting effect on the microorganism.

In one embodiment, the process in accordance with the invention may be operated in a manner such that a fraction of the fermentation mash is withdrawn from the bioreactor, step a) being carried out outside the bioreactor on said fraction, and wherein at least a portion of the fermentation mash which is depleted in fermentation products is recycled to the bioreactor. Alternatively, step a) may be carried out in situ in the bioreactor.

In order to recover the fermentation products present in the gas stream, the process comprises a step c) in which the gas stream which is enriched in fermentation products obtained from step a) is brought into contact with a solvent in a manner such as to produce a solvent which is enriched in fermentation products. Step c) may consist of sending the gas stream which is enriched in fermentation products obtained from step a) to an absorption section in which said gas stream is brought into contact with the organic solvent in a manner such as to recover a gas stream which is depleted in fermentation products and a solvent which is enriched in fermentation products. Advantageously, at least a portion of the gas stream which is depleted in fermentation products is returned to the storage step b).

In accordance with another embodiment, step c) is carried out in the bioreactor which contains the fermentation broth and an organic solvent which is not miscible with water, forming an organic phase floating above the fermentation mash in a manner such that the gas stream which is enriched in fermentation products is brought into contact with the organic solvent in the bioreactor in a manner such as to transfer at least a portion of the fermentation products into said solvent.

The organic solvent may be selected from hydrocarbons with a linear or branched chain, from aromatic hydrocarbons, from carboxylic acids, from alcohols or from esters.

The process in accordance with the invention may comprise a step d) in which the organic solvent which is enriched in fermentation products is recovered and the solvent which is enriched in fermentation products is regenerated in a manner such as to separate said fermentation products and produce a regenerated solvent. Preferably, the regenerated solvent is recycled to step c).

Advantageously, the process in accordance with the invention is applicable to a fermentation mash containing fermentation products selected from esters, ketones, aldehydes, carboxylic acids and alcohols, alone or as a mixture. As an example, the fermentation mash contains butanol, optionally as a mixture with acetone and/or isopropanol and ethanol.

Preferably, the gas stream used as a stripping gas in step a) comprises carbon dioxide, optionally as a mixture with hydrogen. In accordance with the invention, the stripping gas stream constituted by the fermentation gases may be treated before being sent to the bioreactor. The term "treated" designates a step which can be used to eliminate a portion of the compounds which constitute said gas stream. In the context of the invention, the stripping gas may include a prior treatment step in order to minimize its hydrogen content, for example by oxidation or by combustion of hydrogen in an oxidizing medium (for example in the presence of air, pure oxygen, or oxygen supported on a solid acting as an oxidation catalyst).

The process in accordance with the invention may in particular be carried out in order to recover alcohols which may be fermentation-inhibiting products. As an example, beyond a threshold value of approximately 10 g/L, butanol is an inhibitor of fermentation with *Clostridium*. In accordance with one embodiment, step a) is only operated when the fermentation mash has a fermentation products content which is higher than a threshold value.

The invention also concerns a process for the production of fermentation products, comprising the following steps:
 i. in a bioreactor, fermenting an aqueous solution of C5 and/or C6 sugars in the presence of a microorganism in a manner such as to produce a fermentation mash containing fermentation products and fermentation gases;
 ii. sending the fermentation gas produced in the bioreactor to a storage unit;
 iii. sending the stored fermentation gases to the aqueous fermentation broth under pressure in a manner such as to entrain the fermentation products in the gas stream and produce a gas stream which is enriched in fermentation products;
 iv. bringing the gas stream which is enriched in fermentation products into contact with an organic solvent in a manner such as to produce a solvent which is enriched in fermentation products;
 v. regenerating the organic solvent which is enriched in fermentation products in a manner such as to produce a stream which is enriched in fermentation products and a regenerated solvent.

The steps iii) and iv) may be carried out in the bioreactor or outside the bioreactor, while step v) is carried out outside the bioreactor.

In accordance with a preferred embodiment, the fermentation mash contains butanol, optionally mixed with acetone and/or isopropanol and ethanol.

Preferably, the process comprises a step vi) in which a fraction of the fermentation mash is sent to a section for recovery and separation of the fermentation products, said section including at least one distillation unit.

Preferably, the stream enriched in fermentation products obtained from step v) is sent to the section for recovery and separation of the fermentation products.

The process for the production of fermentation products may be applied when the microorganisms are immobilized on a support in the bioreactor.

DETAILED DESCRIPTION OF THE INVENTION

Figure 2:
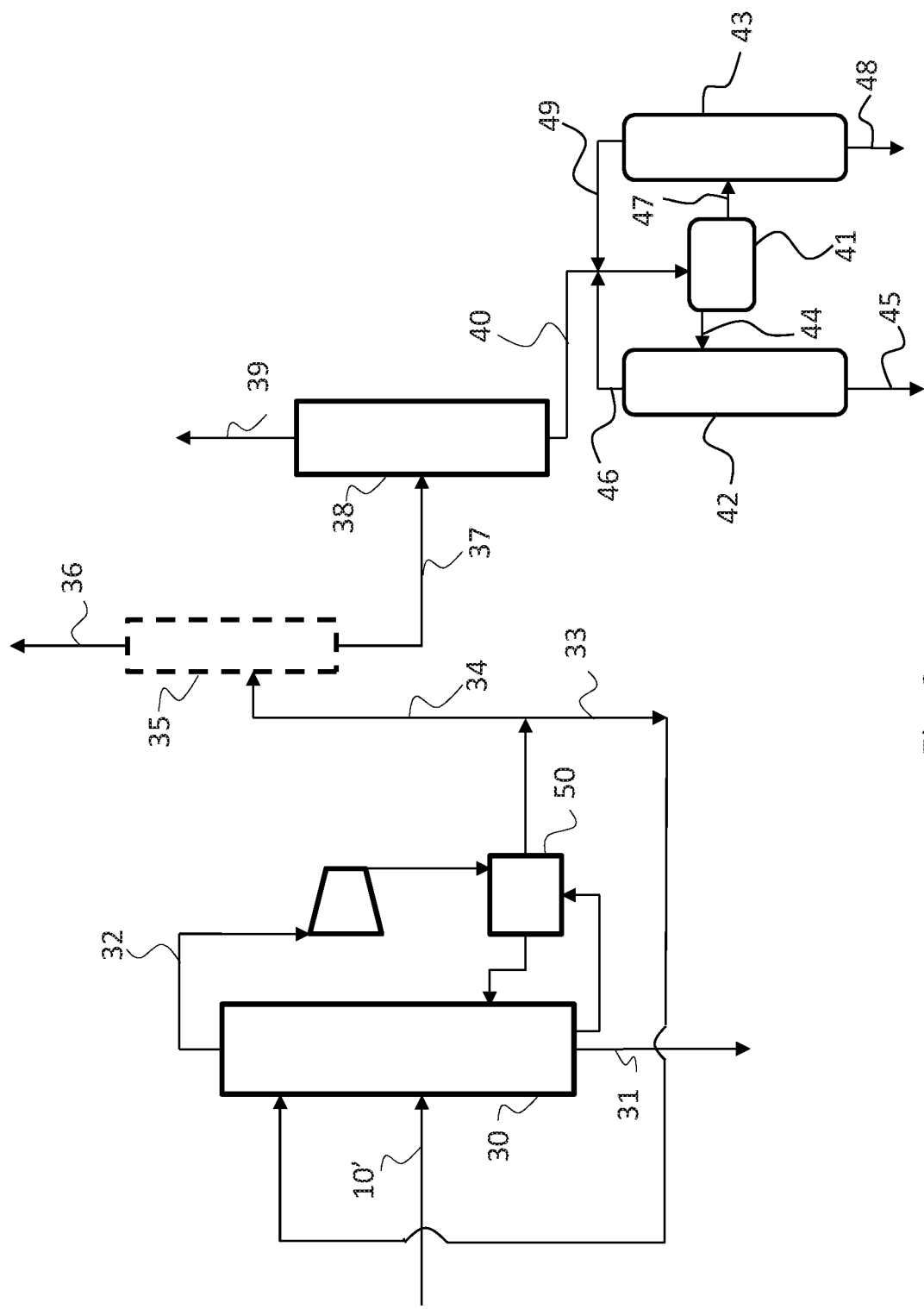

The other characteristics and advantages of the invention will become apparent from the following description, given solely by way of non-limiting illustration and made with reference to:

FIG. 1, which is a process flow diagram for a process for the production of alcohols by fermentation of C5 and/or C6 sugars including a process for the partial recovery of alcohols using the process in accordance with the invention;

FIG. 2, which shows a process flow diagram for a unit for the separation of alcohols produced by fermentation in a bioreactor.

THE FEED

The process in accordance with the invention can be used to treat any fermentation mash (or fermentation broth) which comprises an aqueous phase containing fermentation products and microorganisms. As an example, the fermentation mash may contain a mixture of alcohols containing at least two carbon atoms.

The recovery process is applicable to fermentation broths obtained from an aqueous solution of C5 and/or C6 sugars brought into contact with anaerobic microorganisms which are capable of converting said sugars into alcohols and/or solvents. Preferably, the process in accordance with the invention is used to treat fermentation mashes produced by microorganisms of the genus *Clostridium* (bacterium of the anaerobic gram-positive Bacillaceae family). Preferably, the fermentation microorganism is selected from the strains *Clostridium acetobutylicum* and *Clostridium beijerinckii*, naturally or genetically modified, which are capable of producing solvents of the ABE (Acetone-Butanol-Ethanol) type or of the IBE (Isopropanol-Butanol-Ethanol) type.

For these types of fermentation (ABE or IBE), the process can advantageously be used to extract, continuously or discontinuously, a portion of the alcohols/solvents of interest from the fermentation broth. The process can also be used to limit the content of fermentation products in the fermentation medium for which the presence beyond a threshold value has fermentation-inhibiting effects. As an example, in the case of butanol, this inhibiting effect on *Clostridium* is observed beyond a content of more than 10 g/L.

The aqueous solution of C5 and/or C6 sugars which is fermented may have different origins. It preferably originates from the treatment of a renewable source. Preferably, this source is of the lignocellulosic biomass type, which in particular comprises ligneous substrates (deciduous and softwood), by-products from agriculture (straw) or those from industries generating lignocellulosic waste (agroalimentary, paper industries). The aqueous solution of sugars may also be obtained from sugar crops such as sugar beet and sugar cane, for example, or in fact from starchy plants such as corn or wheat.

FIG. 1 represents a process flow diagram for solvents (mixture of alcohols) from a lignocellulosic biomass type substrate.

With reference to FIG. 1, a biomass feed is brought into the pre-treatment unit 2 via the conduit 1. The biomass feed may be composed of wood, straw or corncobs, products from dedicated forestry crops (for example softwood such as spruce or pine, or deciduous such as eucalyptus), plants from dedicated crops such as miscanthus or switchgrass, residues from alcoholigenic plants, sugar crops (for example sugar cane or beet), and cereals (for example corn, wheat, etc), products and residues from the paper industry and products from the transformation of lignocellulosic materials. The feed may be composed of approximately 35% to 50% by weight of cellulose, 20% to 30% by weight of hemicellulose and 15% to 25% by weight of lignin.

The acidic or basic compound and the water necessary for the pre-treatment are supplied to the pre-treatment unit 2 via conduits (not shown) in order to carry out a hydrolysis reaction in an acidic or basic medium therein. In the unit 2, the biomass feed is brought into contact and mixed with water and the acidic or basic compound in a reactor. The pre-treatment unit 2 may also employ a mechanical action generated, for example, by means of a twin-screw type extruder or a shredder. The acidic compound for the pre-treatment may be selected from sulphuric acid, hydrochloric acid, nitric acid, acetic acid or formic acid. Concerning the basic compound, this may be selected from potassium hydroxide, sodium hydroxide and ammonia.

The pre-treatment unit may employ an AFEX (Ammonia Fibre Explosion) process, which consists of introducing the lignocellulosic substrate into a high-pressure cooker in the presence of ammonia, then causing an explosive depressurization at the outlet from the reactor and recycling the ammonia which is then in the gaseous form. This type of process has been described in particular by Teymouri et al., 2005, Biores. Technol. 96 (2005) p. 2014-2018. This process principally leads to a destructuring of the matrix of the biomass, but there is no phase separation of the lignin, hemicellulose and cellulose compounds at the treatment outlet. In accordance with a second embodiment, an acid pre-treatment is carried out in the unit 2. As an example, a digestion type pre-treatment with dilute acid could be carried out. In this embodiment, the biomass is brought into contact with a strong acid diluted in water, for example sulphuric acid, by using the biomass with low dry matter contents, generally in the range 5% to 20% of dry matter.

The biomass, acid and water are brought into contact in a reactor and the temperature is raised, generally to between 120° C. and 200° C. During this process, the hemicellulose compounds are principally hydrolysed into sugars, meaning that the lignocellulosic matrix can be destructured. At the end of this acid pre-treatment, a solid pre-treated substrate is produced which is enriched in cellulose and lignin, as well as a liquid fraction which is enriched in sugars.

In accordance with a third embodiment, in addition, the "Steam Explosion" or "SteamEx" process may be carried out in the unit 2. This is a process in which the lignocellulosic biomass is brought into contact with water in a reactor for a short dwell time, generally in the range 2 to 15 minutes, and at moderate temperatures, generally between 120° C. and 250° C., and at a pressure in the range 0.5 to 5 MPa (5 to 50 bar). The water may be supplemented with an acidic compound, for example sulphuric acid, or with a basic compound. At the outlet from the reactor, the biomass is depressurized, for example to atmospheric pressure, in a gas/solid separator vessel in order to produce a high dry matter pre-treated biomass, generally in the range 20% to 70% dry matter.

A pre-treated substrate s evacuated from the pre-treatment unit 2 via the conduit 3. The pre-treated substrate is composed of sugars dissolved in the liquid phase and solid material composed of lignin, cellulose and hemicellulose which has not been liquefied during the pre-treatment. The stream of pre-treated substrate moving in the conduit 3 preferably contains in the range 10% by weight and 60% by weight of dry matter, and more preferably in the range 20% by weight to 55% by weight of dry matter.

The pre-treated substrate is introduced into a reactor 4 in order to undergo a step termed "enzymatic hydrolysis". Water and enzymes are respectively added to the reactor 4 in order to carry out an enzymatic hydrolysis reaction on the pre-treated substrate. The quantities of substrate pre-treated with water and enzyme are adjusted in the hydrolysis reactor in a manner such that the reaction medium comprises a solid material content which is generally in the range 5% to 40% by weight, preferably in the range 10% to 25% by weight. The enzymatic hydrolysis is preferably carried out at a pH in the range 4 to 5.5 and at a temperature in the range 35° C. to 60° C. The enzymes may be produced by a microorganism, examples being fungi belonging to the genuses *Trichoderma, Aspergillus, Penicillium* or *Schizophyllum*, or anaerobic bacteria belonging to the genus *Clostridium*, for example. The enzymes produced by these microorganisms in particular contain cellulases and possibly hemicellulases, and are adapted to carry out an intense hydrolysis of the cellulose and possibly of the hemicelluloses. The cellulases or the hemicellulases respectively transform the cellulose or hemicellulose, by hydrolysis into sugars which can dissolve in the aqueous phase. In the enzymatic hydrolysis unit, the operating conditions, principally the dry matter content of the mixture to be hydrolysed and the quantity of enzymes used, are selected in a manner such that a dissolution of the cellulose is obtained which is in the range 20% to 99% by weight, preferably in the range 30% to 95% by weight with respect to the total weight of cellulose contained in the pre-treated substrate. A hydrolysate is evacuated from the hydrolysis reactor 4 via the conduit 5. Thus, the hydrolysate 5 comprises sugars dissolved in an aqueous phase and solid material composed principally of lignin, cellulose and hemicellulose which have not been hydrolysed.

In the unit 6, the hydrolysate 5 may then undergo a step for separation of the liquid and solid in order to extract the solid material therefrom, in particular lignin. The separation of the solid material may employ one of the following techniques: centrifuging, draining or pressing, filtration, or decanting. The unit 6 produces a liquid stream which is depleted in solid material evacuated via the conduit 7, and a stream which is enriched in solid material, in particular in lignin, evacuated via the conduit 8.

The aqueous stream which is depleted in solid and containing C5 and/or C6 sugars is then sent to a fermentation unit 9 via the conduit 7 in order to undergo a fermentation step. In the unit 9, the aqueous stream is then brought into contact with one or more fermentation microorganisms. The microorganisms may, for example, be selected from the following elements: yeasts from the genus *Saccharomyces, Saccharomyces cerevisiae, Schizosaccharomyces pombe, Saccharomyces uvarum, Saccharomyces diastaticus, Kluyveromyces fragilis, Candida shehatae, Pichia stipitis, Pachysolen tannophilis*, or bacteria from the genus *Zymomonas mobilis, Clostridium, Escherichia coli*. The fermentable sugars are then transformed into alcohols and/or solvents by the microorganisms. The fermentation step in the unit 9 may be carried out at a temperature in the range 30° C. to 37° C. in order to produce a fermentation mash (or broth or liquor) containing fermentation reaction products, for example alcohols and/or organic solvents, which is then evacuated via the conduit 10.

The fermentation mash is introduced into a separation unit 11 via the conduit 10 in order to separate and extract the compounds of interest from the fermentation mash, these latter being evacuated via the conduit 12. The separation residues, conventionally known as slops, are evacuated from the separation unit 11 via the conduit 13. The slops are generally composed of water as well as any liquid or solid product which has not been converted or extracted during the preceding steps. The separation unit 11 may carry out one or more distillations, and optionally a separation of the material in suspension, for example by centrifuging, settling, filtration.

Preferably, the fermentation process is a process termed an "ABE" or "IBE" process which can produce an (Acetone-Butanol-Ethanol) or (Isopropanol-Butanol-Ethanol) mixture respectively.

In the context of the invention, the fermentation step may be carried out either in accordance with a semi-continuous operational mode (or "fed-batch" mode), or in accordance with an operational mode known as a continuous mode; these are well known to the person skilled in the art.

It should be noted that the fermentation step may be carried out after the enzymatic hydrolysis step or in fact at the same time as the hydrolysis step ("SSF" or Simultaneous Saccharification and Fermentation type fermentation).

Finally, it is also possible to use a bioreactor in which the fermentation microorganisms are immobilized on a support.

In accordance with an alternative embodiment, the bioreactor may comprise an assembly including a first reactor coupled via a first line to a second reactor in which the fermentation microorganisms are immobilized on a support, and a second line allowing the fermentation mash produced in the second reactor to be recycled to the first reactor. In this embodiment, stripping of the fermentation gas is carried out at the first reactor.

As indicated in FIG. 1, the process for the production of alcohols uses a step for partial recovery of the alcohols produced present in the fermentation mash (or liquor). This step for extracting the alcohols employs a first stripping step with a gas under pressure. As indicated in FIG. 1, a pressurized gas stored in a storage device 14 (for example a drum) is sent via the line 15 to the fermenter 9 in order to entrain the alcohols present in the aqueous phase. In general, the gas is sent to the bioreactor under pressure at a space velocity per minute in the range 0.5 to 3 L/L/min. In accordance with an important characteristic of the invention, the stripping gas is a gas produced directly by fermentation and which has previously been stored before using it. The stripping gas typically comprises carbon dioxide and optionally hydrogen. The recovery step thus uses a gas produced in situ by the fermentation step and thus does not require makeup with a gas from outside said process, thereby limiting the operating costs (OPEX) linked in particular to the purchase and transport of makeup gas. In the context of the invention, the fermentation gases may be stored with one (or more) water-sealed cap gas holders. It could be possible to envisage storage under pressure with prior recompression, typically up to 6 MPa (60 bar). The decompression of the gas used after storage may advantageously compensate for a portion of the energy for compression. The fermentation gas may also be stored in geological cavities of the aquifer type when it contains little hydrogen, this latter having been burned off, for example.

This gas stripping step can advantageously be used to control the content of the alcohols present in the medium during fermentation in order to limit the phenomena of inhibition of microorganisms which arises when the quantity of alcohols reaches a critical value. In accordance with the invention, this gas stripping step may either be carried out continuously or discontinuously. The flow rate of the fermentation gas with respect to the volume of the fermenter is, for example, in the range 0.5 to 2.5 L/L/min, preferably in the range 0.7 to 1.1 L/L/min.

Advantageously, the bioreactor contains fermentation microorganisms which are immobilized on a support in a manner such that during the stripping step, the gases are not able to entrain a portion of the microorganisms present in the fermentation mash.

With reference to FIG. 1, a gas stream which is enriched in alcohols is extracted from the fermenter 9 via the line 16, then is treated in a separation step in order to recover the alcohols contained in the gas stream 16. To this end, the gas stream is sent to a solvent extraction section using at least one absorption column 17.

The gas stream 16 is brought into contact with a solvent or a mixture of solvents supplied via the line 18, preferably as a counter-current, in a manner such as to produce a purified gas stream with a small quantity of alcohols 19 and a stream of solvent which is enriched in alcohols and with a low water content, 20. The solvent may also contain several compounds. Preferably, the solvent used in the gas/liquid extraction step has a boiling temperature which is least 50° C. higher than that of the product to be recovered. The solvent may be selected from hydrocarbon compounds with a linear or branched chain, aromatic hydrocarbon compounds, carboxylic acids, alcohols or esters. Possible solvents which could be cited include vegetable oils (liquid from 30° C.), alcohols containing more than eleven carbon atoms, preferably β-branched, acids containing more than eleven carbon atoms, which may or may not be branched, preferably comprising one or two hydroxyl functions.

The gas stream is brought into contact with a solvent supplied via the line 18, preferably as a counter-current, in a manner such as to produce a purified gas stream 19 with a low alcohols content and a stream of solvent 20 which is enriched in alcohols and which has a low water content.

As indicated in FIG. 1, the purified gas stream 19 is placed under pressure using a compressor 21 and sent to the storage device 14 with a view to being sent once again to the fermenter 9. Regarding the stream of solvent 20 which is enriched in alcohols, it is advantageously treated in a solvent regeneration unit 22 in a manner such as to separate the alcohols from the organic phase. As an example, this regeneration step may be carried out by distillation. The regeneration step produces a stream of alcohol and a stream of regenerated solvent which are evacuated from the regeneration unit 22 via the lines 23 and 24 respectively. The regenerated solvent is then recycled to the extraction section using solvent.

The concentrated stream of alcohols 23, which also has a lower water content than the fermentation mash (typically of the order of 50% by weight), is advantageously mixed with the mash 10 withdrawn from the bioreactor 9 in a mixing zone 25. Said mixture is then treated in the unit 11 for separating alcohols. Compared with a conventional scheme in which only the fermentation mash is treated in the unit 11 for separating alcohols, the step for separating the mixture (fermentation mash+stream concentrated in alcohols) in the unit 11 for separating alcohols requires an energy consumption which is lower for the same alcohol recovery ratio produced because the stream of alcohols treated by said section has a lower water content.

In accordance with another embodiment, the recovery process in accordance with the invention may also be carried out in a manner such that the gas stripping step is operated in a bioreactor 9 containing an organic solvent which is not miscible with water, the solvent forming an organic phase floating above the fermentation mash. In addition, the solvent will be selected in a manner such as to be biocompatible with the microorganism.

The stripping gas is thus injected into the fermentation mash in a manner such as to entrain the alcohols produced in the supernatant organic phase and in a manner such that a portion of the alcohols is transferred into the organic phase when the stripping gas passes through said organic phase. The stripping gas, which still contains alcohols, is withdrawn from the fermenter 9 and is treated in the solvent absorption unit 17 as described above. When the organic phase contained in the fermenter 9 is saturated with alcohols, it is withdrawn and sent to a solvent regeneration unit 22 in order to recover the alcohols and provide a regenerated solvent which is recycled to the fermenter 9. This implementational embodiment thus does not require a continuous solvent regeneration loop. Regarding the organic phase which is enriched in alcohols 20 obtained from the absorption unit, this is advantageously regenerated in the same solvent regeneration unit 22.

This implementational embodiment improves the recovery of alcohols contained in the fermentation mash because the products which are entrained by the stripping gas are immediately brought into contact with the organic phase.

Furthermore, when the process for recovering the fermentation products in accordance with the invention is essentially aimed at controlling the quantity of products in the fermentation medium with a view to limiting the effect of inhibition on the microorganism, this embodiment can in particular be used to reduce the total time for gas stripping when the quantity of solvent and/or the absorption power and/or the selectivity of the solvent (or mixture of solvents) introduced into the bioreactor are selected in a manner such that the threshold value for the concentration of products in the aqueous phase is only reached after saturation of the organic phase.

FIG. 2 shows a process flow diagram of a unit 11 for the separation of the alcohols produced by an IBE type fermentation, i.e. an Isopropanol-Butanol-Ethanol mixture, optionally with acetone.

In a preferred embodiment of the process for the production of fermentation products in accordance with the invention, the aqueous mixture 10' comprising the fermentation mash 10 withdrawn from the bioreactor and the stream which is enriched in alcohols 23 obtained from the solvent regeneration unit 22 is treated in the alcohols separation unit 11. With reference to FIG. 2, the mixture 10' is sent to a first distillation column 30, also termed the "beer column". The column 30 is designed to separate a portion of the water 31 contained in the mixture which is recovered from the bottom of said column. The composition of this water is such that it can be recycled in part directly upstream of the bioreactor, the other portion being sent for water treatment, before in turn being recycled upstream of the fermenter. An aqueous mixture which is enriched in alcohols 32 (IBE, possibly with acetone) is withdrawn from the head of the column 30. The stream recovered from the head of this first column is more concentrated in alcohols than the feed. It is, for example, possible to reach a concentration factor for the alcohols of 25 or more (g/L per g/L).

Preferably, as shown in FIG. 2, the column 30 employs a reboiler system 50 by mechanical recompression of the overhead vapours. This system can be used to reduce the energy requirement for this column by approximately 30% to 50%.

The stream recovered from the head of this first column 30 is recycled in part to the column 30 as a reflux via the line 33. The other, non-recycled, portion 34 of the stream is optionally sent to a second distillation column 35. The role of this second column 35 is to separate the acetone from the stream of alcohols; the acetone is extracted from the head of the column 35 via the line 36, and to produce an aqueous stream which is concentrated in isopropanol-butanol-ethanol which is withdrawn from the bottom via the line 37.

The stream 37 is then sent to a third distillation column 38 designed and operated to separate an overhead mixture 39 containing ethanol/isopropanol/water with an azeotropic composition and an aqueous bottom effluent 40 which is concentrated in butanol. In order to manage the phenomena of demixing which may appear beyond a certain concentration of butanol, the column 38 is preferably equipped with one or more liquid/liquid/vapour demixing zones comprising specific contact means. Alternatively, the column 38 may be operated at a pressure which is slightly higher, in order to dispense with these demixing phenomena.

The water content of the stream 40 may be high or low, as a function of the water content of the treated mixture 10' and the water content of the azeotropic ethanol/isopropanol/water mixture 39 produced overhead from the third column 38. If it is necessary to dry the aqueous stream of butanol 40, this may be treated using a heteroazeotropic distillation system.

As can be seen in FIG. 2, the aqueous stream of butanol 40 is sent to a butanol demixing unit in order to recover the butanol. To this end, the aqueous stream of butanol is cooled, for example to a temperature of 60° C., in a separator drum 41 in order to demix the mixture into two phases, namely an organic phase essentially containing butanol (for example at least 70% by weight of butanol) and an aqueous phase.

The two phases are treated in a heteroazeotropic distillation system which comprises two columns 42, 43 operating in parallel. The organic phase containing mainly butanol is sent via the line 44 to the heteroazeotropic distillation column 42 which functions, for example, at a pressure in the range 0.3 to 10 MPa and at a temperature in the range 115° C. to 150° C. in order to avoid liquid-liquid-vapour demixing problems. An effluent with a content by weight of at least 99% of butanol is withdrawn from the bottom of said column 42 via the line 45, and an aqueous effluent is withdrawn from the head via the line 46 and returned to the separator drum 41.

The aqueous phase still contains butanol, which is withdrawn from the bi-phase separator drum 41 into the heteroazeotropic distillation column 43 via the line 47. From this column 43, respectively, a stream 48 which is rich in water is withdrawn from the bottom and an effluent containing butanol is withdrawn from the head and recycled to the biphase separator drum 41 via the line 49. The column 43 is operated under less severe conditions, for example at a pressure below that of the column 42.

Example

The example below was constructed by simulation using process design and operational analysis software (Simsci Pro/II) which integrates the results obtained from laboratory tests and obtained from the literature concerning fermentation using microorganisms of the genus *Clostridium*.

For the simulation, a fermentation production unit was assumed to use a fermentation unit comprising ten fermenters which treated an aqueous 50 g/L glucose solution. The total volume of the fermentation unit was 10×500 m$^3$, with a total useful volume of 10×400 m$^3$. The initial hypothesis was that the total productivity was 0.54 g/L/h of solvent with an Isopropanol-Butanol-Ethanol percentage weight distribution of 28%/62%/10%. The production unit then produced 17000 t/year of IBE mixture, i.e. approximately 4800 t/year of isopropanol, 10560 t/year of butanol and 1600 t/year of ethanol.

The consumption of sugar in the factory was approximately 53000 t/year of glucose, assuming a yield of 0.32 g of IBE/g of sugar.

The fermenters operated at 37° C. in batch mode for 34 hours, following which inhibition by butanol occurred.

The final composition of the fermentation mash obtained from the fermenters was as follows: 4.8 g/L of isopropanol, 10.5 g/L of butanol and 1.7 g/L of ethanol, i.e. approximately 17 g/L of IBE products in the fermentation mash.

Starting from the hypothesis that the energy necessary for separating the alcohols contained in the fermentation mash on the one hand and for separating the butanol from the isopropanol+ethanol mixture (directly upgradable in petrochemistry) on the other hand was approximately 20 MJ/kg of IBE mixture, the consumption of steam was estimated to be approximately 150000 t/year of steam (i.e. approximately 8.8 t of vapour/t of IBE mixture).

The natural fermentation process liberated 12000 Nm$^3$/h, assuming that the flow rate of gas (in litres per minute) with respect to the volume of the fermenter (in litres) was 0.05 L/L/min of gas, which was a mixture essentially comprising $CO_2$ and $H_2$ which was not used as a stripping gas.

Example in Accordance with the Invention

The process in accordance with the invention was carried out in the same unit as that described above which comprised ten IBE fermenters.

The fermenters underwent stripping with fermentation gas when the concentration of the metabolite inhibitor butanol in the fermentation medium was at least 80% of the inhibition threshold (fixed at 10 g/L of butanol). The stripping was carried out with a flow rate of gas (in litres per minute) with respect to the volume of the fermenter (in litres) of 1 L/L/min, i.e. 240000 Nm$^3$/h of fermentation gas. This fermentation gas had been stored, for example from the commencement of fermentation, in order to have a sufficient volume available.

In order to limit the phenomenon of knocking during injection of the fermentation gas for stripping, it is preferable to provide a reserve of fermentation gas which is equivalent to at least 3 minutes injection for a given flow rate.

Fermentation gas continued to be produced at a flow rate of 12000 Nm$^3$/h and was stored in the storage unit and optionally purged when the fermentation gas was in excess compared with the quantity necessary for stripping. The fermentation stripping gas containing the alcohols was sent to a separation unit for the alcohols which involved contacting said gas with a liquid vegetable oil at 37° C. (for example rape, palm or sunflower). The effluents produced by the step for separating the alcohols were a vegetable oil charged with alcohols and a fermentation gas depleted in alcohols. This latter was advantageously recycled as the stripping gas. The vegetable oil containing the alcohols produced was sent to a distillation column operated under vacuum so that the oil was not thermally degraded. Oil purified of the alcohols was recovered from the bottom of this column, and an aqueous mixture of alcohols was recovered overhead. Finally, this stream, concentrated in alcohols, was mixed with the mash remaining in the fermenters at the end of fermentation.

Extraction with the fermentation gas by stripping the most inhibiting product, i.e. butanol in the present case, has several effects:

1. Regarding Productivity

Given that the most inhibiting metabolite is eliminated progressively, the *Clostridium* strain increases its overall productivity which is of the order of 0.94 g of IBE/L/h. Thus, approximately 30000 t/year of IBE mixture could be produced, i.e. approximately 7300 t/year of isopropanol, 20500 t/year of butanol and 2200 t/year of ethanol. The production of the unit was increased by approximately 75%.

2. Regarding the Yield

Relatively less sugar was required to increase the production. The yield was estimated to be 0.4 g of IBE/g of glucose (i.e. an increase of 25% in the yield), which implies a consumption of 75000 t/year of glucose.

3. Separation Energy

The final fermentation mash still contained approximately 17 g/L of IBE mixture, with approximately 4 g/L of isopropanol, 11.6 g/L of butanol and 1.4 g/L of ethanol. However, 90% of the alcohols produced were recovered by the steps for stripping, contacting with a solvent and regeneration of the solvent. The fact of sending the alcohols obtained from the regeneration step to the final mash recovered from the fermenters meant that the energy costs linked to final separation of the butanol could be substantially reduced. Thus, taking into account the energy for distillation of the vegetable oil on the one hand (2 MJ/kg of IBE mixture) and separation of butanol from the isopropanol+ethanol mixture (5 MJ/kg of IBE mixture) on the other hand, the steam consumption was estimated to be approximately 93000 t/year of steam, i.e. approximately 3.1 t of steam/t of IBE mixture, giving an energy reduction of approximately 65%.

4. Extending Cycle Time

Because inhibition was removed by eliminating butanol from the mash, the fermentations could be operated in fed-batch mode or continuously, which had the advantage of extending the operating time by approximately 500 hours.

The invention claimed is:

1. A process for recovering fermentation products present in a fermentation mash, which fermentation mash has been produced in a bioreactor, comprising
    storing fermentation gases that have been produced in the bioreactor,
    sending said stored fermentation gases as a gas stream into the fermentation mash under sufficient pressure to entrain at least a portion of the fermentation products and thereby produce a gas stream which is enriched in fermentation products, and
    bringing said gas stream which is enriched in fermentation products into contact with a solvent so as to produce a solvent which is enriched in fermentation products.

2. The process as claimed in claim 1, in which a fraction of the fermentation mash is withdrawn from the bioreactor, wherein the sending of said stored fermentation gases as a gas stream under sufficient pressure is into said fraction of the fermentation mash to entrain at least a portion of the fermentation products and thereby produce a gas stream which is enriched in fermentation products and a fermentation mash which is depleted in fermentation products, wherein at least of portion of the fermentation mash depleted in fermentation products is recycled to the bioreactor.

3. The process as claimed in claim 1, in which the sending of said stored fermentation gases as a gas stream into the fermentation mash under sufficient pressure to entrain at least a portion of the fermentation products and thereby produce a gas stream which is enriched in fermentation products is carried out in the bioreactor.

4. The process as claimed in claim 1, in which the bringing into contact of the gas stream which is enriched in fermentation products with a solvent to produce a solvent which is enriched in fermentation products is carried out by sending said gas stream which is enriched in fermentation products to a gas/liquid absorption section in which said gas stream is brought into contact with the solvent to produce the solvent which is enriched in fermentation products and a gas stream which is depleted in fermentation products.

5. The process as claimed in claim 1, in which step c) is carried out in the bioreactor, wherein the solvent is an organic solvent which is not miscible with water, and which solvent forms an organic phase floating above the fermentation mash wherein the gas stream which is enriched in fermentation products is brought into contact with the solvent in the organic phase floating above the fermentation mash in the bioreactor to transfer at least a portion of the fermentation products into said solvent.

6. The process as claimed in claim 1, further comprising regenerating the solvent which is enriched in fermentation products to separate said fermentation products from the solvent and thereby produce a regenerated solvent.

7. The process as claimed in claim 1, in which the fermentation mash contains fermentation products selected from the group consisting of esters, ketones, aldehydes, carboxylic acids, alcohols and mixtures thereof.

8. The process as claimed in claim 7, in which the fermentation mash contains butanol, optionally as a mixture with acetone and/or isopropanol and ethanol.

9. The process as claimed in claim 1, in which the gas stream comprises carbon dioxide, optionally as a mixture with hydrogen.

10. The process as claimed in claim 1, in which the gas stream is treated before being sent to the bioreactor.

11. The process as claimed in claim 1, in which the solvent is selected from the group consisting of hydrocarbons with a linear or branched chain, aromatic hydrocarbons, carboxylic acids, alcohols and esters.

12. A process for the production of fermentation products, comprising the following steps:
    i. fermenting an aqueous solution of C5 and/or C6 sugars in a bioreactor in the presence of a microorganism so as to produce a fermentation mash containing fermentation products and fermentation gases;
    ii. sending the fermentation gas produced in the bioreactor to a storage unit;
    iii. sending the stored fermentation gases to the aqueous fermentation broth under sufficient pressure to entrain the fermentation products in the gas stream and thereby produce a gas stream which is enriched in fermentation products;
    iv. bringing said gas stream which is enriched in fermentation products into contact with an organic solvent so as to produce a solvent which is enriched in fermentation products;
    v. regenerating said organic solvent which is enriched in fermentation products so as to produce a stream which is enriched in fermentation products and a regenerated solvent.

13. The process as claimed in claim 12, in which the steps iii) and iv) are carried out in the bioreactor or outside the bioreactor, and in which step v) is carried out outside the bioreactor.

14. The process as claimed in claim 12, in which the fermentation mash contains butanol, optionally mixed with acetone and/or isopropanol and ethanol.

15. The process as claimed in claim 12, further comprising a step vi) in which a fraction of the fermentation mash is sent to a section for recovery and separation of the fermentation products, said section including at least one distillation unit.

16. The process as claimed in claim 15, in which the stream enriched in fermentation products obtained from step v) is sent to the section for recovery and separation of the fermentation products as a mixture with the fraction of fermentation mash.

17. The process as claimed in claim 12, in which the microorganisms are immobilized on a support in the bioreactor.

18. The process as claimed in claim 1, wherein the solvent is an organic solvent.

* * * * *